(12) United States Patent
Choi et al.

(10) Patent No.: US 11,372,067 B2
(45) Date of Patent: Jun. 28, 2022

(54) METHOD FOR ACQUIRING WATER-FAT SEPARATION IMAGE, AND MAGNETIC RESONANCE IMAGING APPARATUS THEREFOR

(71) Applicant: Samsung Electronics Co., Ltd., Suwon-si (KR)

(72) Inventors: Joon-sung Choi, Anyang-si (KR); Hyun-sang Suh, Suwon-si (KR); Hyun-seok Seo, Seoul (KR); Myung-sung Song, Hwaseong-si (KR); Dae-ho Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 106 days.

(21) Appl. No.: 16/770,287

(22) PCT Filed: Aug. 7, 2018

(86) PCT No.: PCT/KR2018/008923
§ 371 (c)(1),
(2) Date: Jun. 5, 2020

(87) PCT Pub. No.: WO2019/117417
PCT Pub. Date: Jun. 20, 2019

(65) Prior Publication Data
US 2021/0173030 A1    Jun. 10, 2021

(30) Foreign Application Priority Data
Dec. 11, 2017 (KR) .................. 10-2017-0169530

(51) Int. Cl.
*G01V 3/00* (2006.01)
*G01R 33/48* (2006.01)
(Continued)

(52) U.S. Cl.
CPC .......... *G01R 33/4828* (2013.01); *A61B 5/055* (2013.01); *A61B 5/4872* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 6,249,595 B1    6/2001  Foxall et al.
6,560,353 B1    5/2003  Haacke et al.
(Continued)

FOREIGN PATENT DOCUMENTS

KR    10-2014-0001779 A    1/2014
KR    10-2015-0027706 A    3/2015
(Continued)

OTHER PUBLICATIONS

Frank Ong et al., "General Phase Regularized Reconstruction with Phase Cycling", *Proceedings of the International Society for Magnetic Resonance in Medicine*, Apr. 7, 2017, vol. 25, 1201**.
(Continued)

*Primary Examiner* — Walter L Lindsay, Jr.
*Assistant Examiner* — Frederick Wenderoth
(74) *Attorney, Agent, or Firm* — Staas & Halsey LLP

(57) ABSTRACT

Provided are a method of obtaining a water-fat separation image and a magnetic resonance imaging (MRI) apparatus including a controller configured to obtain first partial k-space data, second partial k-space data, and third partial k-space data, respectively based on a first partial echo signal, a second partial echo signal, and a third partial echo signal, which are magnetic resonance signals corresponding to a plurality of echo times with respect to an object, obtain first reconstruction image data, second reconstruction image
(Continued)

data, and third reconstruction image data with respect to the object, respectively based on the first partial k-space data, the second partial k-space data, and the third partial k-space data, and obtain first water image data, first fat image data, and first phase image data of the object, respectively based on the first reconstruction image data, the second reconstruction image data, and the third reconstruction image data, by using a Dixon technique.

18 Claims, 10 Drawing Sheets

(51) Int. Cl.
    *A61B 5/055*     (2006.01)
    *A61B 5/00*     (2006.01)
    *G01R 33/561*     (2006.01)
    *G06T 11/00*     (2006.01)

(52) U.S. Cl.
    CPC ........ *A61B 5/4875* (2013.01); *G01R 33/4818* (2013.01); *G01R 33/5615* (2013.01); *G06T 11/006* (2013.01); *G06T 11/008* (2013.01); *G06T 2210/41* (2013.01)

(58) Field of Classification Search
    USPC .......................................................... 324/309
    See application file for complete search history.

(56) References Cited

U.S. PATENT DOCUMENTS

| | | | |
|---|---|---|---|
| 7,277,597 B2 | 10/2007 | Lee et al. | |
| 9,390,476 B2 | 7/2016 | Weng | |
| 9,753,109 B2* | 9/2017 | Eggers | G01R 33/4828 |
| 9,823,322 B2 | 11/2017 | Kannengiesser et al. | |
| 10,185,013 B2 | 1/2019 | Park et al. | |
| 10,451,696 B2 | 10/2019 | Suh | |
| 2006/0250132 A1* | 11/2006 | Reeder | G01R 33/4828 |
| | | | 324/307 |
| 2007/0276224 A1* | 11/2007 | Lang | A61B 5/1038 |
| | | | 600/410 |
| 2015/0161800 A1* | 6/2015 | Nagae | A61B 6/504 |
| | | | 378/62 |
| 2015/0323637 A1* | 11/2015 | Beck | G01R 33/5676 |
| | | | 600/410 |
| 2016/0033606 A1 | 2/2016 | Eggers | |
| 2016/0161580 A1* | 6/2016 | Shirai | G01R 33/543 |
| | | | 324/322 |
| 2016/0216352 A1 | 7/2016 | Eggers et al. | |
| 2017/0131374 A1 | 5/2017 | Choi et al. | |
| 2017/0131377 A1 | 5/2017 | Kim et al. | |

FOREIGN PATENT DOCUMENTS

| | | |
|---|---|---|
| KR | 10-2016-0114447 A | 10/2016 |
| KR | 10-2017-0054977 A | 5/2017 |
| KR | 10-2017-0054984 A | 5/2017 |
| KR | 10-1775028 B1 | 9/2017 |

OTHER PUBLICATIONS

Scott B. Reeder et al., "Cardiac CINE Imaging with IDEAL Water-Fat Separation and Steady-State Free Precession", *Journal of Magnetic Resonance Imaging*, Jul. 1, 2005, vol. 22, No. 1, pp. 44-52**.

Scott B. Reeder et al., "Multicoil Dixon Chemical Species Separation with an Iterative Least-Squares Estimation Method", *Magnetic Resonance in Medicine*, Jan. 1, 2004, vol. 51, No. 1, pp. 35-45**.

Extended European Search dated Jan. 26, 2021, in corresponding European Patent Application No. 18888616.2.

G. H. Glover et al., "Three-point Dixon Technique for True water/fat Decomposition with $B_0$ Inhomogeneity Correction", *Magn Reson Med.*, Apr. 1991, 18(2):371-83.

E.M. Haacke et at., "A fast, iterative, partial-fourier technique capable of local phase recovery", *Journal of Magnetic Resonance* (1969) vol. 92, Issue 1, Mar. 1991, p. 126-p. 145.

International Search Report dated Nov. 8, 2018, in corresponding International Patent Application No. PCT/KR2018/008923.

Office Action dated Jun. 20, 2019, in corresponding Korean Patent Application No. 10-2017-0169530.

Notice of Allowance dated Oct. 8, 2019, in corresponding Korean Patent Application No. 10-2017-0169530.

* cited by examiner

FIG. 3A $$\begin{bmatrix} k_0 \\ k_1 \\ k_{-1} \end{bmatrix} = \begin{bmatrix} \mathit{fft}((w+f)e^{j\phi_0}) \\ \mathit{fft}((w-f)e^{j(\phi_0+\phi)}) \\ \mathit{fft}((w-f)e^{j(\phi_0-\phi)}) \end{bmatrix} \quad \text{—310}$$

⇓ Dixon $w, f, \phi_0, \phi$ —315

METHOD FOR ACQUIRING WATER-FAT SEPARATION IMAGE, AND MAGNETIC RESONANCE IMAGING APPARATUS THEREFOR

CROSS-REFERENCE TO RELATED APPLICATIONS

This application is a U.S. National Stage Application which claims the benefit under 35 U.S.C. § 371 of International Patent Application No. PCT/KR2018/008923 filed on Aug. 7, 2018, which claims foreign priority benefit under 35 U.S.C. § 119 of Korean Patent Application No. 10-2017-0169530 filed on Dec. 11, 2017, in the Korean Intellectual Property Office, the contents of both of which are incorporated herein by reference.

TECHNICAL FIELD

The disclosure relates to a method of obtaining a water-fat separation image and a magnetic resonance imaging (MRI) apparatus. More specifically, the disclosure relates to a method of obtaining a water-fat separation image using a Dixon technique and an MRI apparatus.

BACKGROUND ART

A magnetic resonance imaging (MRI) apparatus images an object using a magnetic field. Because the MRI apparatus is capable of creating three-dimensional images of bones, discs, joints, ligaments, or the like at a user-desired angle, the MRI apparatus is widely used to make a correct disease diagnosis.

The MRI apparatus acquires a magnetic resonance (MR) signal, reconstructs the obtained MR signal into an image, and outputs the image. In more detail, the MRI apparatus acquires the MR signal using a high-frequency multi-coil including radio frequency (RF) coils, permanent-magnets, superconducting magnets, gradient coils, etc.

Specifically, a high frequency signal generated by applying a pulse sequence for generating a radio frequency signal to a high frequency multi coil is applied to an object, and a MR image is reconstructed by sampling a magnetic resonance signal generated in response to the applied high-frequency signal.

Meanwhile, a MR signal of interest in most clinical pathologies is a MR signal of water obtained from hydrogen atoms in the object. However, hydrogen is also included in fat as well as in water, and a MR signal of relatively strong fat interferes with a MR signal of relatively weak water. Accordingly, various imaging techniques have been used to obtain a water-fat separation image in order to obtain a relatively clear MR signal of water.

One such water-fat separation imaging technique is the Dixon technique. The Dixon technique is a technique that separates MR signals of water and fat after obtaining a plurality of data having different echo times (TE) using features of different Lamor frequencies of water and fat. Meanwhile, in the Dixon technique, there is a problem in that it takes a long time to obtain a plurality of data because the plurality of data must be obtained in order to separate MR signals of water and fat.

DESCRIPTION OF EMBODIMENTS

Technical Problem

Provided are a method capable of reducing an acquisition time of a water-fat separation image and a magnetic resonance imaging (MRI) apparatus.

Solution to Problem

According to an aspect of the disclosure, a magnetic resonance imaging (MRI) apparatus for obtaining a water-fat separation image includes a controller configured to obtain first partial k-space data, second partial k-space data, and third partial k-space data, based on a first partial echo signal, a second partial echo signal, and a third partial echo signal, which are magnetic resonance signals corresponding to a plurality of echo times with respect to an object, obtain first reconstruction image data, second reconstruction image data, and third reconstruction image data with respect to the object, based on the first partial k-space data, the second partial k-space data, and the third partial k-space data, and obtain first water image data, first fat image data, and first phase image data of the object, based on the first reconstruction image data, the second reconstruction image data, and the third reconstruction image data, using a Dixon technique.

According to another aspect of the disclosure, a method of obtaining a water-fat separation image includes obtaining first partial k-space data, second partial k-space data, and third partial k-space data, based on a first partial echo signal, a second partial echo signal, and a third partial echo signal, which are magnetic resonance signals corresponding to a plurality of echo times with respect to an object; obtaining first reconstruction image data, second reconstruction image data, and third reconstruction image data with respect to the object, based on the first partial k-space data, the second partial k-space data, and the third partial k-space data; and obtaining first water image data, first fat image data, and first phase image data of the object, based on the first reconstruction image data, the second reconstruction image data, and the third reconstruction image data, using a Dixon technique.

According to another aspect of the disclosure, a computer program product comprising a computer readable recording medium having recorded thereon a program for executing the method described above on a computer is provided.

BRIEF DESCRIPTION OF DRAWINGS

FIGS. 3A and 3B are diagrams for describing an operation, performed by an MRI apparatus, of obtaining water-fat separation image data using a Dixon technique, according to an embodiment.

MODE OF DISCLOSURE

Figure 1:
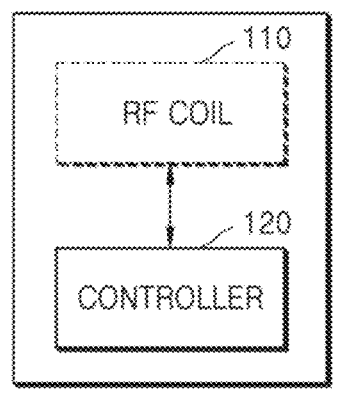
FIG. 1 is a block diagram illustrating a magnetic resonance imaging (MRI) apparatus, according to an embodiment.

The present specification describes principles of the disclosure and sets forth embodiments thereof to clarify the scope of the disclosure and to allow those of ordinary skill in the art to implement the embodiments. The present embodiments may have different forms.

Like reference numerals refer to like elements throughout. The present specification does not describe all components in the embodiments, and common knowledge in the art or the same descriptions of the embodiments will be omitted below. The term "part" or "portion" may be implemented using hardware or software, and according to embodiments, one "part" or "portion" may be formed as a single unit or element or include a plurality of units or elements. Hereinafter, the principles and embodiments of the disclosure will be described in detail with reference to the accompanying drawings.

In the present specification, an "image" may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part (an organ) or a phantom.

An MRI system acquires an MR signal and reconstructs the obtained MR signal into an image. The MR signal denotes a radio frequency (RF) signal emitted from the object.

In the MRI system, a main magnet creates a static magnetic field to align a magnetic dipole moment of a specific atomic nucleus of the object placed in the static magnetic field along a direction of the static magnetic field. A gradient coil may generate a gradient magnetic field by applying a gradient signal to a static magnetic field and induce resonance frequencies differently according to each region of the object.

An RF coil may emit an RF signal to match a resonance frequency of a region of the object whose image is to be obtained. Furthermore, when gradient magnetic fields are applied, the RF coil may receive MR signals having different resonance frequencies emitted from a plurality of regions of the object. Though this process, the MRI system may obtain an image from an MR signal using an image reconstruction technique.

FIG. 1 is a block diagram illustrating a magnetic resonance imaging (MRI) apparatus 100, according to an embodiment.

According to an embodiment, the MRI apparatus 100 may include all image processing apparatuses capable of obtaining an MR image based on MR image data obtained by MRI capturing. In addition, the MRI apparatus 100 may include a computing device capable of controlling the acquisition of MR image data in MRI capturing.

Referring to FIG. 1, the MRI apparatus 100 according to an embodiment may include an RF coil 110 and a controller 120. However, the components of the MRI apparatus 100 are not limited to the components shown in FIG. 1. According to an embodiment, the MRI apparatus 100 may be implemented by fewer components or by more components than the components shown in FIG. 1. For example, the MRI apparatus 100 may not include the RF coil 110 among the components shown in FIG. 1. In this case, the MRI apparatus 100 may be a device for obtaining a MRI signal obtained by an external device including an RF coil.

The RF coil 110 may include one or more components for radiating an RF signal to an object under the control of the controller 120. For example, the RF coil 110 may include a plurality of RF channels. In addition, the RF coil 110 may receive MR signals emitted from the object and provide the MR signals to the controller 120.

According to an embodiment, the controller 120 may control the RF coil 110 such that at least one RF excitation pulse and at least one RF refocusing pulse are irradiated to the object. For example, the controller 120 may determine the size, direction, and timing at which the at least one RF excitation pulse and the at least one refocusing pulse are irradiated to the object, and transmit a control signal corresponding to determined information to the RF coil 110.

For example, the controller 120 may determine the size, direction, and timing at which the RF excitation pulse and the RF refocusing pulse are irradiated to the object based on a spin echo (SE) technique. Here, the spin echo technique may be a technique that as a 90-degree RF excitation pulse is irradiated to a specific tissue of an object, when dephasing of atoms in the specific tissue is performed, a 180-degree refocusing pulse is irradiated to the object and thus an echo signal (i.e., a MR signal) is received using magnetization caused when atoms in the tissue perform in-phase precession in an opposite direction.

According to an embodiment, the controller 120 may control the RF coil 110 to receive a plurality of echo signals at a time corresponding to each of a plurality of echo times (TEs). Here, the TE may mean a time from when the RF pulse is irradiated to the object to a time when the echo signal is measured.

Specifically, the controller 120 may control the RF coil 110 to irradiate the RF excitation pulse to the object and to receive MR signals respectively corresponding to the plurality of echo times (TEs) from the object. For example, the plurality of echo times (TEs) may include a first TE, a second TE, and a third TE. The first TE, the second TE, and the third TE may be different values from each other. In addition, the MR signals respectively corresponding to the plurality of TEs may include a first partial echo signal, a second partial echo signal, and a third partial echo signal. Here, the partial echo signal may be an echo signal corresponding to a part of k-space data.

The controller 120 may obtain a first partial echo signal, a second partial echo signal, and a third partial echo signal, which are MR signals respectively corresponding to the plurality of TEs with respect to the object. In addition, the controller 120 may respectively obtain first partial k-space data, second partial k-space data, and third partial k-space data based on the first partial echo signal, the second partial echo signal, and the third partial echo signal. The controller 120 may perform Fourier transform on each of the first partial echo signal, the second partial echo signal, and the third partial echo signal to respectively obtain the first partial k-space data, the second partial k-space data, and the third partial k-space data.

The controller 120 may respectively obtain first reconstruction image data, second reconstruction image data, and third reconstruction image data with respect to the object based on the first partial k-spatial data, the second partial k-spatial data, and the third partial k-spatial data. The controller 120 may reconstruct the remaining part of partial k-space data obtained from only a part of the k-space data using a partial Fourier technique.

Here, the partial Fourier technique may be a technique of reconstructing the remaining part of the partial k-space data obtained from only the part of the k-space data using 1) the feature that when MRI data includes only a real value, the k-space data obtained by Fourier transforming the MRI data is symmetric about the origin with respect to the k-space, and 2) the feature that a phase component of the MRI data includes only a low frequency component having no large change. More specifically, the partial Fourier technique reconstructs MRI data of a region that is not obtained using origin symmetry of the obtained k-space data of the partial echo signal based on the feature that the k-space data obtained by Fourier transforming the MRI data establishes the relationship k(r)=conjugate(k(−r)) when the MRI data includes only a real value. However, when the MRI data includes a complex value including an imaginary value in addition to the real value, the k-space data of the MRI data no longer establish the relationship k(r)=conjugate(k(−r)). In this case, the partial Fourier technique infers and removes the phase component based on the low frequency data of the k-space data of the partial echo signal based on the feature that only the low frequency component is included in the phase component of the MRI data, and reconstructs MRI data of a K-space region that is not obtained based on a magnitude component that is a real value satisfying the relationship k(r)=conjugate(k(−r)). Such partial Fourier techniques may include, for example, POCS, homodyne reconstruction technique, and the like.

The controller 120 may obtain first water image data, first fat image data, and first phase image of the object based on the first reconstruction image data, the second reconstruction image data, and the third reconstruction image data using the Dixon technique. Here, the Dixon technique may be a technique for obtaining water image data, fat image data, and phase image data based on MRI data obtained at different echo times (e.g., TE, TE+Δt, TE−Δt).

For example, the controller 120 may obtain water image data w, fat image data f, and phase image data ϕ and ϕ₀ corresponding to variables based on three equations of Mathematical Equation 1 below. In Mathematical Equation 1 below, $S_0$ may denote first reconstruction image data corresponding to the first partial echo signal obtained at TE, $S_1$ may denote second reconstruction image data corresponding to the second partial echo signal obtained at TE+Δt, and $S_{-1}$ may denote third reconstruction image data corresponding to the third partial echo signal obtained at TE−Δt. In addition, of the phase image data included in Mathematical Equation 1 below, ϕ may be phase image data by a static magnetic field ($B_0$ field), and ϕ₀ may be phase image data by a system. According to an embodiment, when the controller 120 uses a spin echo sequence, since the spin echo sequence includes a sequence that compensates for the phase change caused by the static magnetic field, $S_0$ obtained at the TE may not include ϕ.

$$S_0 = (w+f)\angle\phi_0$$
$$S_1 = (w-f)\angle(\phi_0+\phi)$$
$$S_{n1} = (w-f)\angle(\phi_0-\phi)$$ [Mathematical Equation]1

According to an embodiment, the controller 120 may obtain at least one of a first water emphasis image, a first fat emphasis image, and a first phase image based on the obtained first water image data, first fat image data, and first phase image data. In addition, the controller 120 may control a display (not shown) to display at least one of the obtained first water emphasis image, first fat emphasis image, and first phase image.

According to the embodiments, the MRI apparatus 100 may use the partial Fourier technique and the Dixon technique to obtain the water image data and the fat image data, thereby reducing the time taken to obtain the water-fat separation image.

Figure 2:
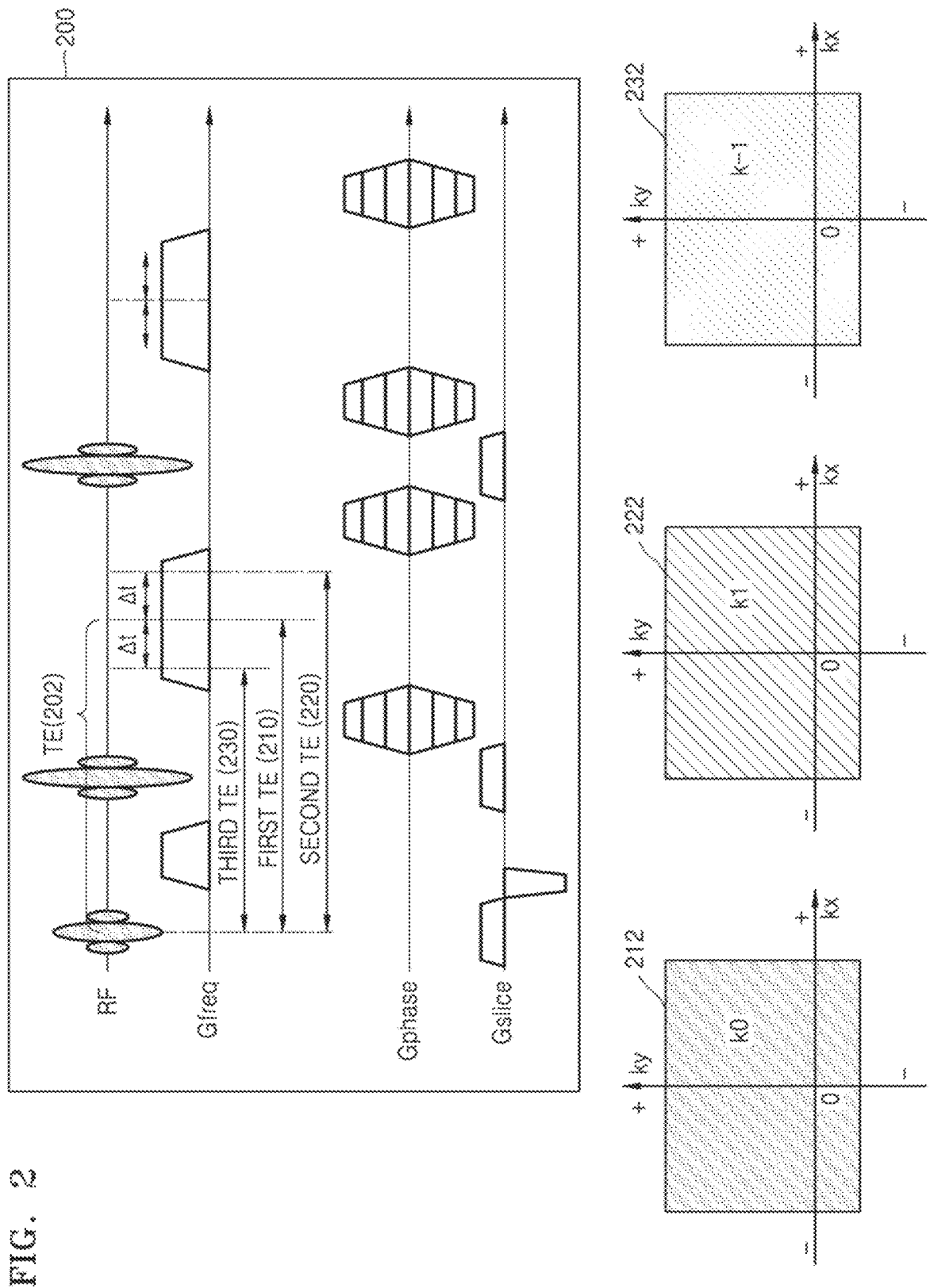
FIG. 2 is a diagram for describing an operation, performed by an MRI apparatus, of obtaining a plurality of partial echo signals respectively corresponding to a plurality of echo times, according to an embodiment.

FIG. 2 is a diagram for describing an operation, performed by the MRI apparatus 100, of obtaining a plurality of partial echo signals respectively corresponding to a plurality of echo times, according to an embodiment.

Referring to FIG. 2, a sequence diagram 200 for the MRI apparatus 100 to obtain the plurality of partial echo signals respectively corresponding to the plurality of echo times is shown, according to an embodiment.

According to an embodiment, the MRI apparatus 100 may use a spin echo sequence to obtain first water image data, first fat image data, and first phase image data. The sequence diagram 200 illustrated in FIG. 2 may be a sequence corresponding to the spin echo sequence. In addition, a TE 202 of the sequence diagram 200 may correspond to an echo time of the spin echo sequence.

In addition, the MRI apparatus 100 may obtain a first partial echo signal, a second partial echo signal, and a third partial echo signal, respectively, corresponding to a first TE (=TE (202)) 210, a second TE (=TE (202)+Δt) 220, and a third TE (=TE (202)−Δt) 230.

In addition, the MRI apparatus 100 may perform Fourier transform on each of the first partial echo signal, the second partial echo signal, and the third partial echo signal to respectively obtain first k-space partial data 212, second k-space partial data 222, and third k-space partial data 232.

The MRI apparatus 100 may reconstruct the first k-space partial data 212, the second k-space partial data 222, and the third k-space partial data 232 which are obtained from only a part of the entire k-space data, using various techniques (e.g., POCS). In the present specification, data obtained by reconstructing first k-space partial data 212, second k-space partial data 222, and third k-space partial data 232 may respectively correspond to first reconstruction image data, second reconstruction image data, and third reconstruction image data.

In addition, the MRI apparatus 100 may use the first reconstruction image data, the second reconstruction image data, and the third reconstruction image data as input data of the Dixon technique for obtaining the first water image data, the first fat image data, and the first phase image data.

According to the embodiments, the MRI apparatus 100 may use the first reconstruction image data, the second reconstruction image data, and the third reconstruction image data obtained by the partial Fourier technique as the input data of the Dixon technique, thereby reducing an acquisition time of a water-fat separation image.

Figure 3B:
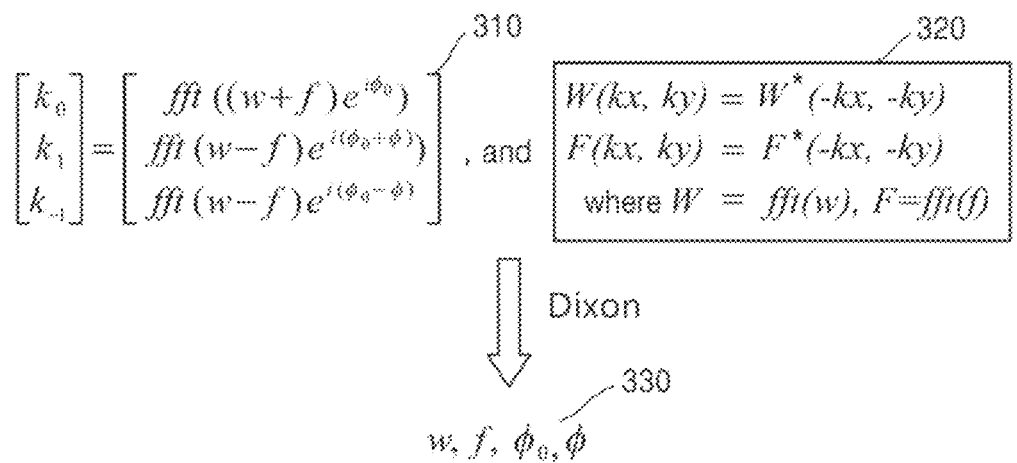

FIGS. 3A and 3B are diagrams for describing an operation, performed by the MRI apparatus 100, of obtaining water-fat separation image data using the Dixon technique, according to an embodiment.

Referring to FIG. 3A, an example in which the MRI apparatus 100 acquires output data 315 based on input data 310 using the Dixon technique according to an embodiment is illustrated.

For example, the input data 310 of the Dixon technique may include $k_0$, $k_1$, and $k_{-1}$ which are k-space data obtained by performing Fourier transforming (FFT) on first reconstruction image data, second reconstruction image data, and third reconstruction image data described above with reference to FIG. 2.

The MRI apparatus 100 may solve three equations for $k_0$, $k_1$, and $k_{-1}$ included in the input data 310 to obtain four unknown which are the first water image data w, the first fat image data f, and the first phase image data $\phi_0$ and $\phi$.

Referring to FIG. 3B, an example in which the MRI apparatus 100 acquires output data 330 based on the input data 310 and an output data condition 320 using the Dixon technique according to another embodiment is illustrated.

The MRI apparatus 100 according to an embodiment illustrated in FIG. 3B may obtain the output data 330 by additionally considering the output data condition 320 compared to the embodiment described above with reference to FIG. 3A.

For example, when the first reconstruction image data, the second reconstruction image data, and the third reconstruction image data which are reconstructed based on the partial Fourier technique are used as input data of the Dixon technique, the quality of a water-fat separation image obtained based on the output data 315 of the Dixon technique may deteriorate.

The reason why the quality of the obtained water-fat separation image deteriorates is as follows. In general, the partial Fourier technique reconstructs data that is not obtained as k-space data with respect to a partial echo signal, based on the feature that phase data of obtained MRI data includes only a low frequency component having no large change. However, a plurality of partial echo signals obtained at a plurality of echo times TE for obtaining the water-fat separation image may further include not only the phase image data $\phi$ by a static magnetic field but also the phase image data $\phi_0$ by a system (see Mathematical Equation 1). In addition, the assumption that the phase image data $\phi$ by the static magnetic field does not have a relatively large change in value and thus includes only a low frequency component may be established, whereas the assumption that the phase image data $\phi_0$ by the system has a relatively large change in value and thus includes only a low frequency component which applied to the partial Fourier technique is not established. Accordingly, the first reconstruction image data, the second reconstruction image data, and the third reconstruction image data which are reconstructed by applying the partial Fourier technique to the plurality of partial echo signals obtained at the plurality of echo times TE for obtaining the water-fat separation image may include artifacts. Accordingly, artifacts may also occur in the water-fat separation image obtained using the Dixon technique based on the first reconstruction image data, the second reconstruction image data, and the third reconstruction image data which include artifacts, which may deteriorate the quality of image.

Accordingly, the MRI apparatus 100 according to an embodiment may apply the additional output data condition 320 such that an origin symmetry feature of the k-space data, which is a real number used for image reconstruction of the partial Fourier technique, despite the phase image data $\phi_0$ by the system is established. The output data condition 320 may include a condition that the k-space data corresponding to each of the first water image data and the first fat image data which are included in the first reconstruction image data, the second reconstruction image data, and the third reconstruction image data which are reconstructed based on the partial Fourier technique is origin symmetry with respect to the center of k-space.

The MRI apparatus 100 may obtain the output data 330 that satisfies both the input data 310 and the output data condition 320 using the Dixon technique. The MRI apparatus 100 may obtain the first water image data and the first fat image data such that the k-space data with respect to the first water image data and the first fat image data which are obtained when obtaining the water-fat separation image using the partial Fourier technique and the Dixon technique is origin symmetry with respect to the k-space. Accordingly, the MRI apparatus 100 may use both the partial Fourier technique and the Dixon technique to reduce the water-fat separation image acquisition time and prevent deterioration of the quality of the obtained water-fat separation image.

Figure 4:
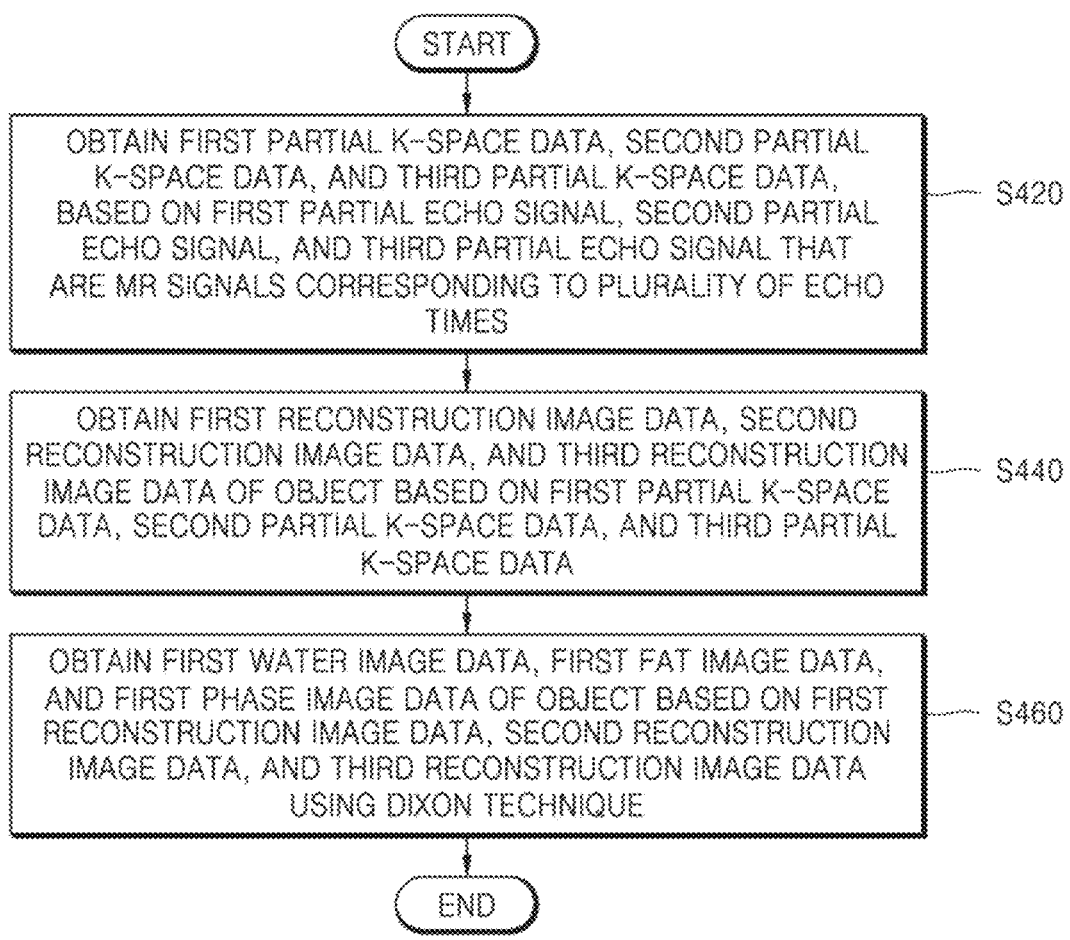
FIG. 4 is a flowchart illustrating a method, performed by an MRI apparatus, of obtaining water-fat separation image data, according to an embodiment.

FIG. 4 is a flowchart illustrating a method, performed by the MRI apparatus 100, of obtaining water-fat separation image data, according to an embodiment.

Referring to FIG. 4, in operation S420, the MRI apparatus 100 according to an embodiment may respectively obtain first partial k-space data, second partial k-space data, and third partial k-space data, based on a first partial echo signal, a second partial echo signal, and a third partial echo signal that are MR signals corresponding to a plurality of echo times.

In an embodiment, the MRI apparatus 100 may respectively obtain a first partial echo signal, a second partial echo signal, and a third partial echo signal corresponding to a plurality of echo times including a first TE, a second TE, and a third TE. Here, the first TE, the second TE, and the third TE may have different values from each other. In addition, the partial echo signal may be an echo signal corresponding to a part of k-space data.

In addition, the MRI apparatus 100 may perform Fourier transform on each of the first partial echo signal, the second partial echo signal, and the third partial echo signal to obtain first partial k-space data, second partial k-space data, and third partial k-space data respectively corresponding to the first partial echo signal, the second partial echo signal, and the third partial echo signal.

In operation S440, the MRI apparatus 100 according to an embodiment may respectively obtain first reconstruction image data, second reconstruction image data, and third reconstruction image data of an object based on the first partial k-space data, the second partial k-space data, and the third partial k-space data.

In an embodiment, the MRI apparatus 100 may use a partial Fourier technique to obtain the first reconstruction image data, the second reconstruction image data, and the third reconstruction image data respectively corresponding to the first partial k-space data, the second partial k-space data, and the third partial k-space data. The MRI apparatus 100 may use the partial Fourier technique to reconstruct the remaining part of the partial k-space data obtained from only a part of the k-space data.

In operation S460, the MRI apparatus 100 according to an embodiment may obtain first water image data, first fat image data, and first phase image data of the object based on the first reconstruction image data, the second reconstruction image data, and the third reconstruction image data using the Dixon technique.

For example, the first reconstruction image data $S_0$, the second reconstruction image data $S_1$, and the third reconstruction image data $S_{n1}$ may be expressed by Mathematical Equation 2 below.

$$S_0 = (w+f)\angle \phi_0$$

$$S_1 = (w-f)\angle(\phi_0+\phi)$$

$$S_{n1} = (w-f)\angle(\phi_0-\phi) \quad \text{[Mathematical Equation 2]}$$

The MRI apparatus 100 may obtain the first water image data w, the first fat image data f, and the first phase image data $\phi$ and $\phi_0$ that satisfy three equations included in Mathematical Equation 2 above.

According to an embodiment, the MRI apparatus 100 may obtain the first water image data w and the first fat image data f based on an additional condition, to increase the quality of the water-fat separation image based on the obtained first water image data w and first fat image data f. For example, the MRI apparatus 100 may obtain first water image data, first fat image data, and first phase image data that cause the k-space data corresponding to each of the first water image data and the first fat image data obtained using the Dixon technique to be origin symmetric with respect to the center of the k-space. In another example, the MRI apparatus 100 may obtain first water image data, first fat image data, and first phase image data such that the k-space data corresponding to each of the first water image data and the first fat image data has an origin symmetric law to be equal to or greater than a certain value (e.g. 95%).

Various embodiments may be applied to the operation performed by the MRI apparatus 100 of obtaining the first water image data, the first fat image data, and the first phase image data that cause the k-space data corresponding to each of the first water image data and the first fat image data to be origin symmetric with respect to the center of the k-space.

As an embodiment in this regard, the MRI apparatus 100 may obtain first k-space data, second k-space data, and third k-space data of the object corresponding to the plurality of echo times based on the first water image data and the first fat image data obtained using the Dixon technique, the first partial k-space data, the second partial k-space data, and the third partial k-space data. The first k-space data, the second k-space data, and the third k-space data may be data reconfigured by combining the first water image data and the first fat image data reconstructed by the partial Fourier technique and the Dixon technique and the first partial image, the second partial k-space data, and the third partial k-space data which are original data of the object. Detailed descriptions related to the operation performed by the MRI apparatus 100 of obtaining the first k-space data, the second k-space data, and the third k-space data will be provided later with reference to FIGS. 5 and 6.

Figure 5:
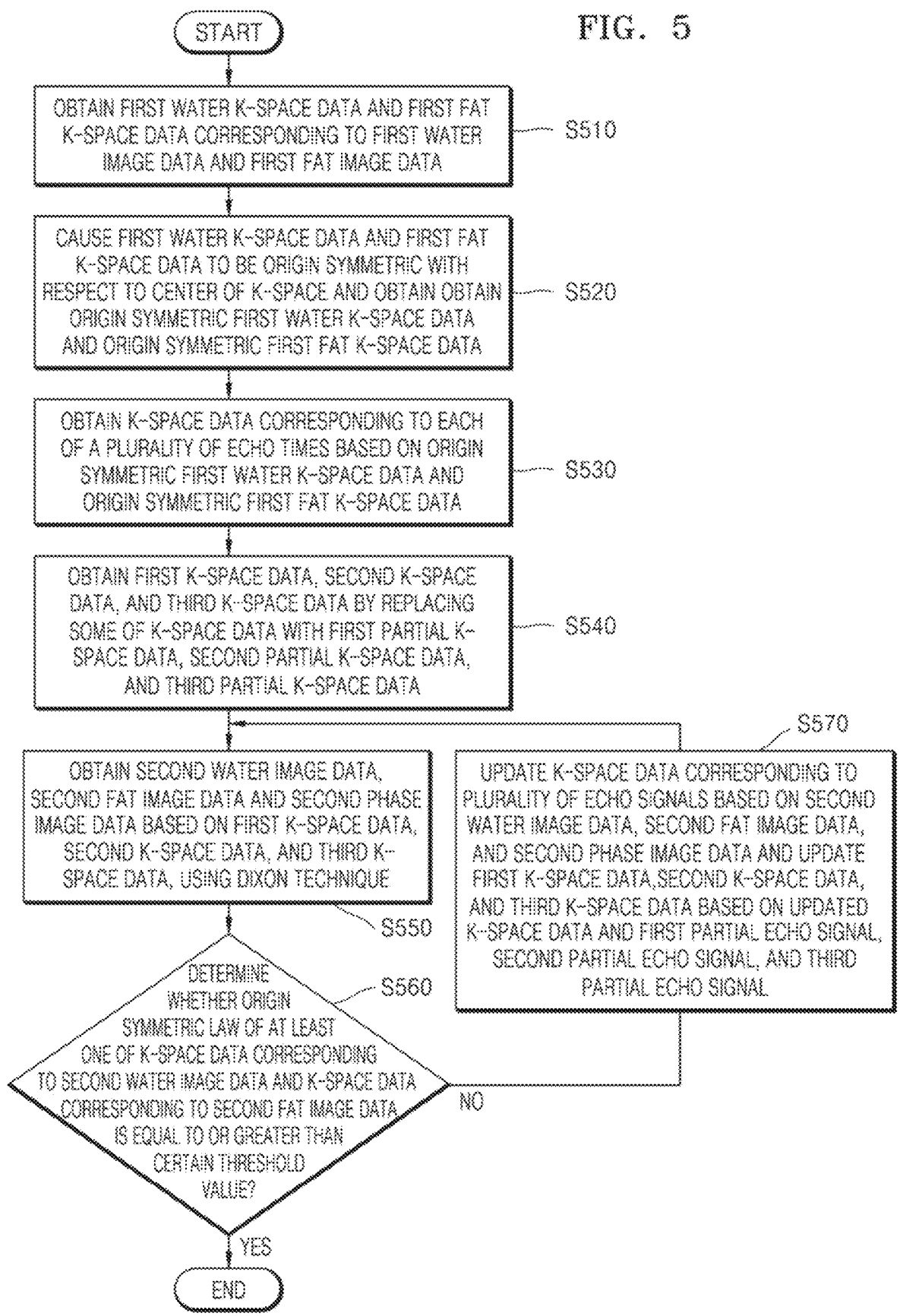
FIG. 5 is a flowchart illustrating a method, performed by an MRI apparatus, of obtaining water-fat separation image data, according to an embodiment.

FIG. 5 is a flowchart illustrating a method, performed by the MRI apparatus 100, of obtaining water-fat separation image data, according to an embodiment.

Referring to FIG. 5, a process that may be additionally performed by the MRI apparatus 100 after first water image data, first fat image data, and first phase image data are obtained based on the partial Fourier technique and the Dixon technique is shown.

In operation S510, the MRI apparatus 100 according to an embodiment may obtain first water k-space data and first fat k-space data respectively corresponding to the first water image data and the first fat image data.

In operation S520, the MRI apparatus 100 according to an embodiment may cause the first water k-space data and the first fat k-space data to be origin symmetric with respect to the center of k-space and obtain the origin symmetric first water k-space data and the origin symmetric first fat k-space data.

In operation S530, the MRI apparatus 100 according to an embodiment may obtain k-space data corresponding to each of a plurality of echo times based on the origin symmetric first water k-space data and the origin symmetric first fat k-space data.

In operation S540, the MRI apparatus 100 according to an embodiment may obtain first k-space data, second k-space data, and third k-space data by replacing some of the k-space data obtained in operation S530 with first partial k-space data, second partial k-space data, and third partial k-space data.

In an embodiment, the MRI apparatus 100 may use a mask in a process of obtaining the first k-space data, the second k-space data, and the third k-space data. Here, the mask may be a mask in which a region where data is obtained as the first spatial k-space data, the second partial k-space data, and the third partial k-space data in the k-space data is filled with '1', and a region where data is not obtained is filled with '0'. The MRI apparatus 100 may obtain the first k-space data, the second k-space data, and the third k-space data by replacing parts of the k-space data obtained in operation S520 corresponding to the first partial k-space data, the second partial k-space data, and the third partial k-space data with the first partial k-space data, the second partial k-space data, and the third partial k-space data, using the mask.

In operation S550, the MRI apparatus 100 according to an embodiment may obtain second water image data, second fat image data and second phase image data based on the first k-space data, the second k-space data, and the third k-space data, using the Dixon technique.

In operation S560, the MRI apparatus 100 may determine whether an origin symmetric law of at least one of k-space data corresponding to the second water image data and k-space data corresponding to the second fat image data is equal to or greater than a certain threshold value.

In an embodiment, when the origin symmetric law of at least one of k-space data corresponding to the second water image data and k-space data corresponding to the second fat image data is greater than the certain threshold value, the MRI apparatus 100 may end the process. In addition, the MRI apparatus 100 may obtain a water-fat separation image based on the obtained second water image data and second fat image data.

In another embodiment, when the origin symmetric law of at least one of k-space data corresponding to the second water image data and k-space data corresponding to the second fat image data is less than the certain threshold value, in operation S570, the MRI apparatus 100 may update the k-space data corresponding to the plurality of echo signals based on the second water image data, the second fat image data, and the second phase image data. In addition, the MRI apparatus 100 may update the first k-space data, the second k-space data, and the third k-space data based on the updated k-space data and the first partial echo signal, the second partial echo signal, and the third partial echo signal.

In FIG. 5, it is described that the MRI apparatus 100 repeats operations S550 to S570 based on the origin symmetric law of at least one of the k-space data corresponding to the second water image data and the k-space data corresponding to the second fat image data, but the embodiment is not limited thereto.

In another embodiment, the MRI apparatus 100 may obtain the second water image data and the second fat image data by repeating operations S550 and S570 a certain number of times without a process of determining the origin symmetric law.

In another embodiment, the MRI apparatus 100 may end the process when the second water image data and the second fat image data obtained by repeating operations S550 and S570 are converged to a specific data value, and a data change value obtained by repeating operations S550 and S570 is equal to or less than a certain value and obtain the second water image data and the second fat image data.

Figure 6:
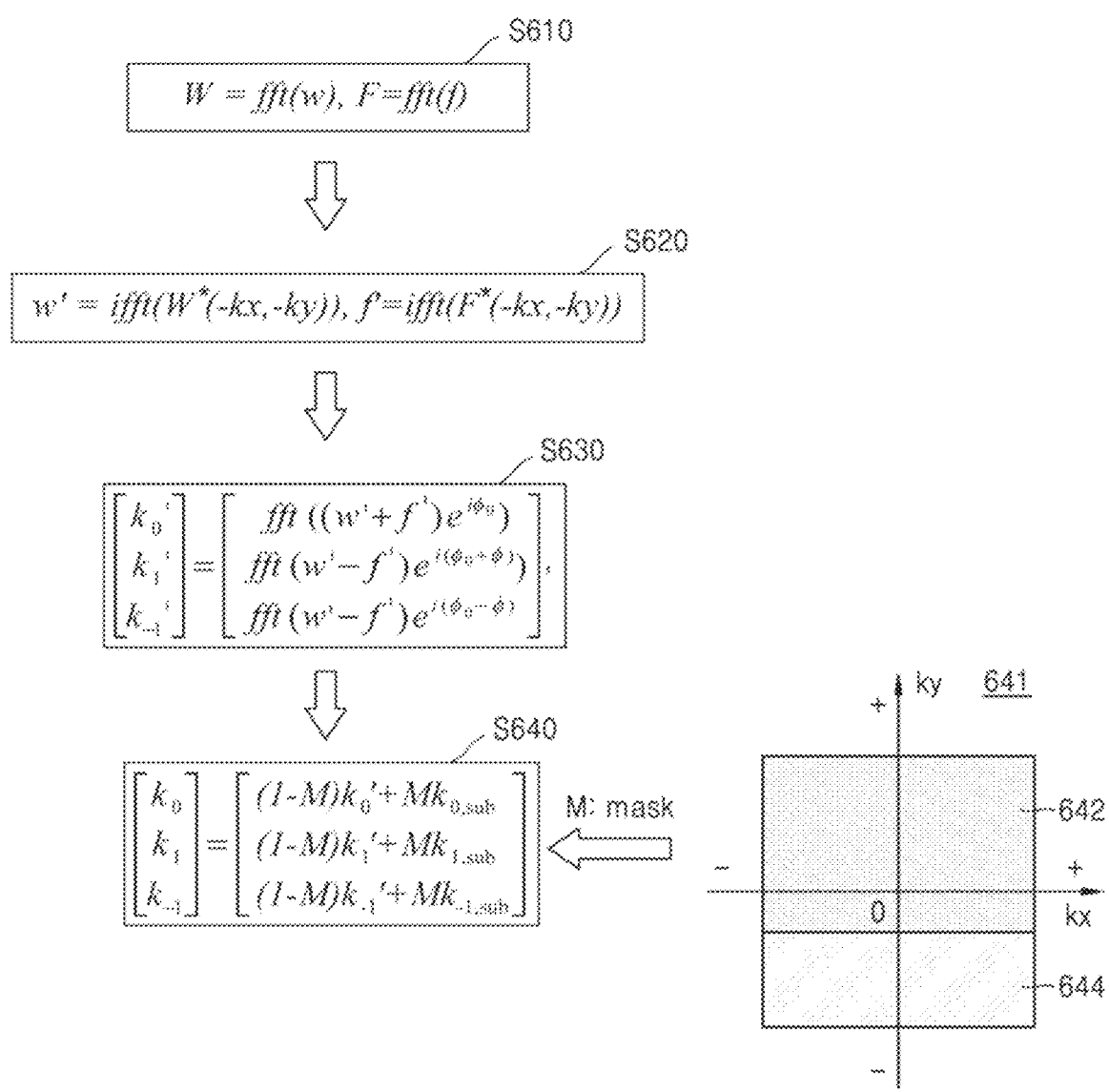
FIG. 6 is a diagram for describing an operation, by an MRI apparatus, of updating k-space data for obtaining water-fat separation image data using a Dixon technique, according to an embodiment.

FIG. 6 is a diagram for describing an operation, by the MRI apparatus 100, of updating k-space data for obtaining water-fat separation image data using the Dixon technique, according to an embodiment.

FIG. 6 is a diagram representing operations S510 to S540 described above with reference to FIG. 5 in a corresponding equation.

Referring to FIG. 6, in operation S610, the MRI apparatus 100 according to an embodiment may obtain first water k-space data (W=fft(w)) and first fat k-space data (F=fft(f)) corresponding to the first water image data w and the first fat image data f, respectively. In addition, operation S610 may be an operation corresponding to operation S510 shown in FIG. 5.

In operation S620, the MRI apparatus 100 according to an embodiment may cause each of first water k-space data W and first fat k-space data F to be origin symmetric with respect to the center of the k-space to obtain the origin symmetric first water k-space data (W*(-kx,-ky)) and the origin symmetric first fat k-space data (F*(-kx,-ky)). In addition, the MRI apparatus 100 may perform inverse Fourier transform on each of the origin symmetric first water k-space data (W*(-kx,-ky)) and the origin symmetric first fat k-space data (F*(-kx,-ky)) to obtain origin symmetric first water image data w' and origin symmetric first fat image data f'. Operation S620 may be an operation including operation S520 illustrated in FIG. 5.

In operation S630, the MRI apparatus 100 according to an embodiment may obtain k-space data $k_0'$, $k_1'$, and $k_{-1}'$ respectively corresponding to a plurality of echo times, based on the origin symmetric first water image data w', the origin symmetric first fat image data f', and the first phase image data. Operation S630 may be an operation including operation S530 illustrated in FIG. 5.

In operation S640, the MRI apparatus 100 according to an embodiment may obtain first k-space data $k_0$, the second k-space data $k_1$ and third k-space data $k_{-1}$, based on the k-space data $k_0'$, $k_1'$, and $k_{-1}'$ respectively corresponding to the plurality of echo times and first partial k-space data $k_{0,sub}$, second partial k-space data $k_{1,sub}$, and third partial k-space data $k_{-1,sub}$. Operation S640 may be an operation including operation S560 illustrated in FIG. 5.

According to an embodiment, the MRI apparatus 100 may obtain a certain mask 641 to obtain the first k-space data $k_0$, the second k-space data $k_1$ and the third k-space data $k_{-1}$. The mask 641 may be data corresponding to k-space data in which a first region 642 is filled with '1' and a second region 644 is filled with '0'. In addition, the first region 642 may be a region corresponding to a part of the k-space data where data is obtained as each of the first partial k-space data, the second partial k-space data, and the third partial k-space data. The MRI apparatus 100 may use the mask 641 to respectively obtain the first k-space data $k_0$, the second k-space data $k_1$ and third k-space data $k_{-1}$ by replacing a part of each of the k-space data $k_0'$, $k_1'$, and $k_{-1}'$ where data is obtained as each of the first partial k-space data, the second partial k-space data, and the third partial k-space data with each of the first partial k-space data, the second partial k-space data, and the third partial k-space data.

Figure 7A:
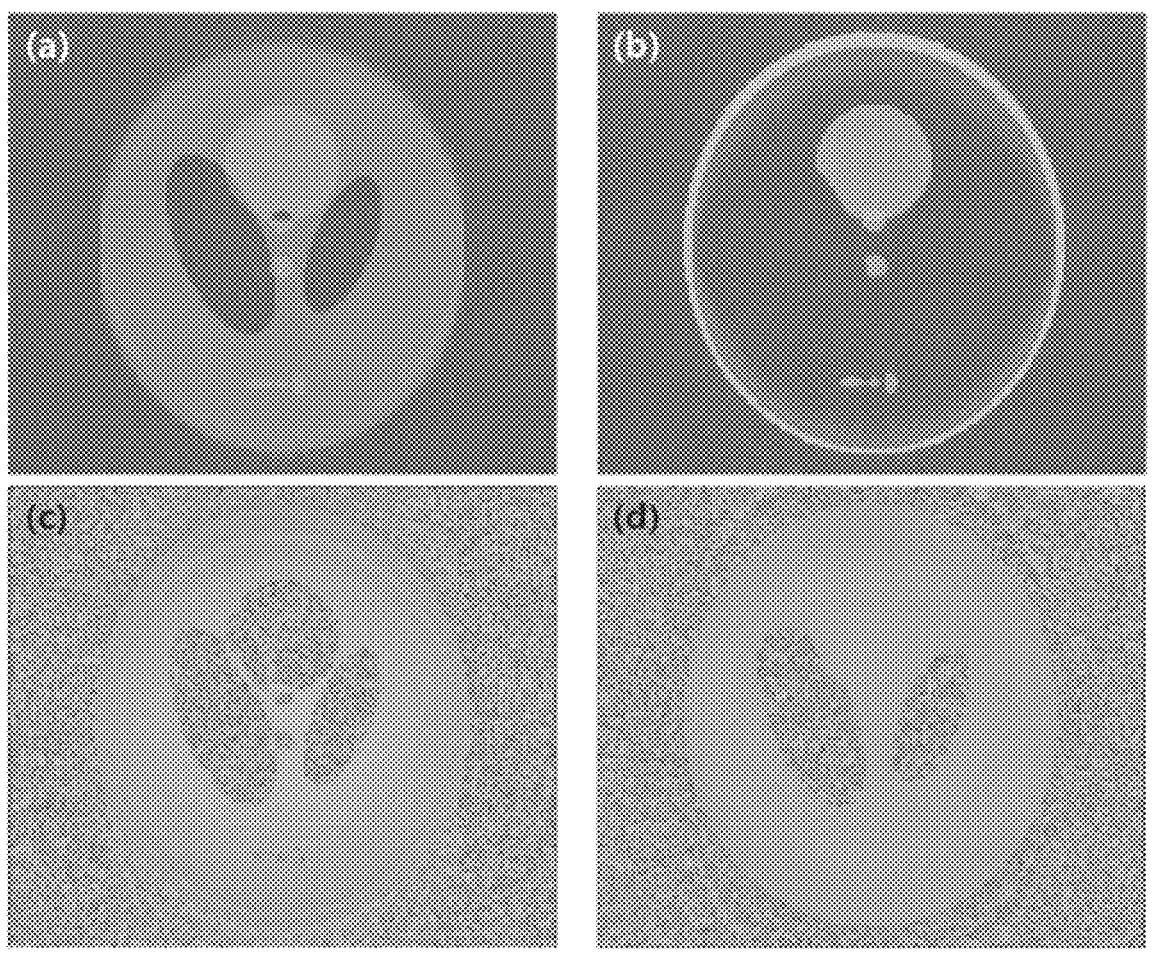
FIGS. 7A and 7B are diagrams showing experimental results of water-fat separation images and phase images obtained according to embodiments.
Figure 7B:
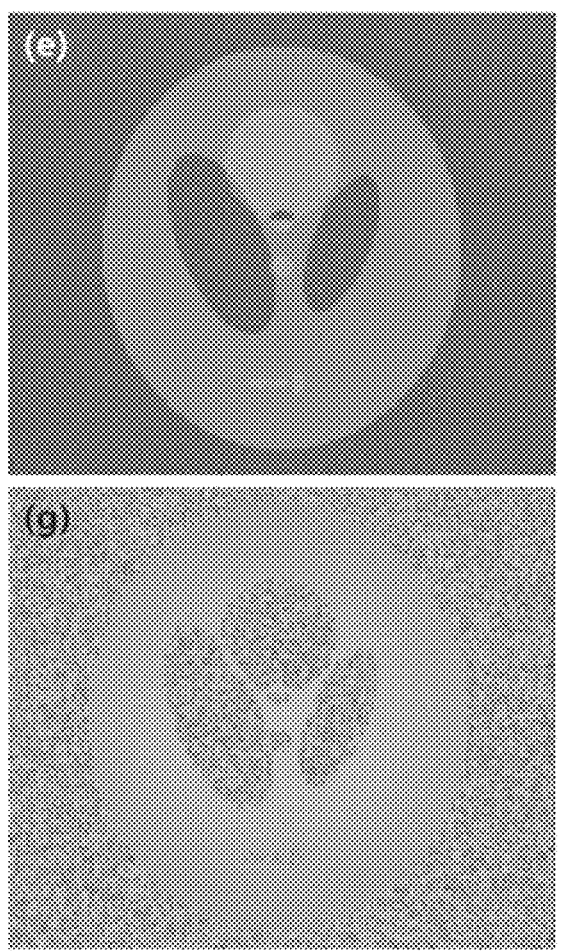
Figure 7B:
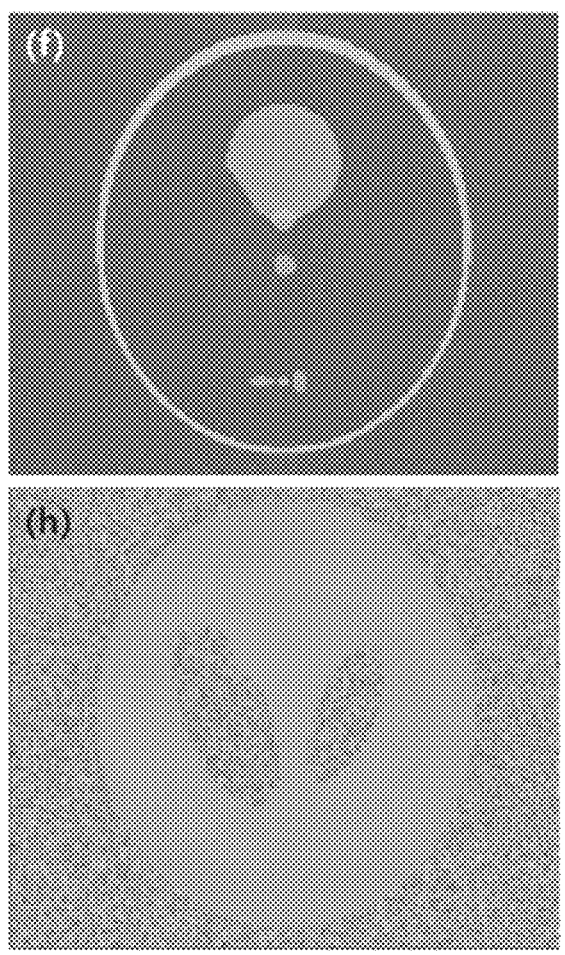

FIGS. 7A and 7B are diagrams showing experimental results of water-fat separation images and phase images obtained according to embodiments.

Referring to FIG. 7A, (a) a water emphasis image, (b) a fat emphasis image, (c) a phase image by a static magnetic field, and (d) a phase image by a system obtained based on an embodiment described above in FIG. 3A are shown. In addition, referring to FIG. 7B, (e) a water emphasis image, (f) a fat emphasis image, (g) a phase image by a static magnetic field, and (h) a phase image by a system obtained based on another embodiment described above with reference to FIG. 3B are shown.

Upon comparing (a) the water emphasis image and (e) the water emphasis image shown in FIGS. 7A and 7B, respectively, it may be seen that more artifacts are reduced in (e) the water emphasis image. In addition, similarly, it may be seen that (f) the fat emphasis image, (g) the phase image by the static magnetic field, and (h) the phase image by the system shown in FIG. 7B are images with improved artifacts respectively compared to (b) the fat emphasis image, (c) the phase image by the static magnetic field, and (d) the phase image by the system shown in FIG. 7A.

As such, the MRI apparatus 100 according to the embodiments may accelerate the acquisition time of the water-fat separation image using the partial Fourier technique and the Dixon technique.

In addition, the MRI apparatus 100 according to the embodiments may obtain the first k-space data, the second k-space data, and the third k-space data by repeatedly reconfiguring the first water image data, the first fat image data, and the first phase image data that are obtained using the partial Fourier technique and the Dixon technique based on the first partial k-space data, the second partial k-space data, and the third partial k-space data, thereby reducing artifacts caused by combining and using the partial Fourier technique and the Dixon technique.

Figure 8:
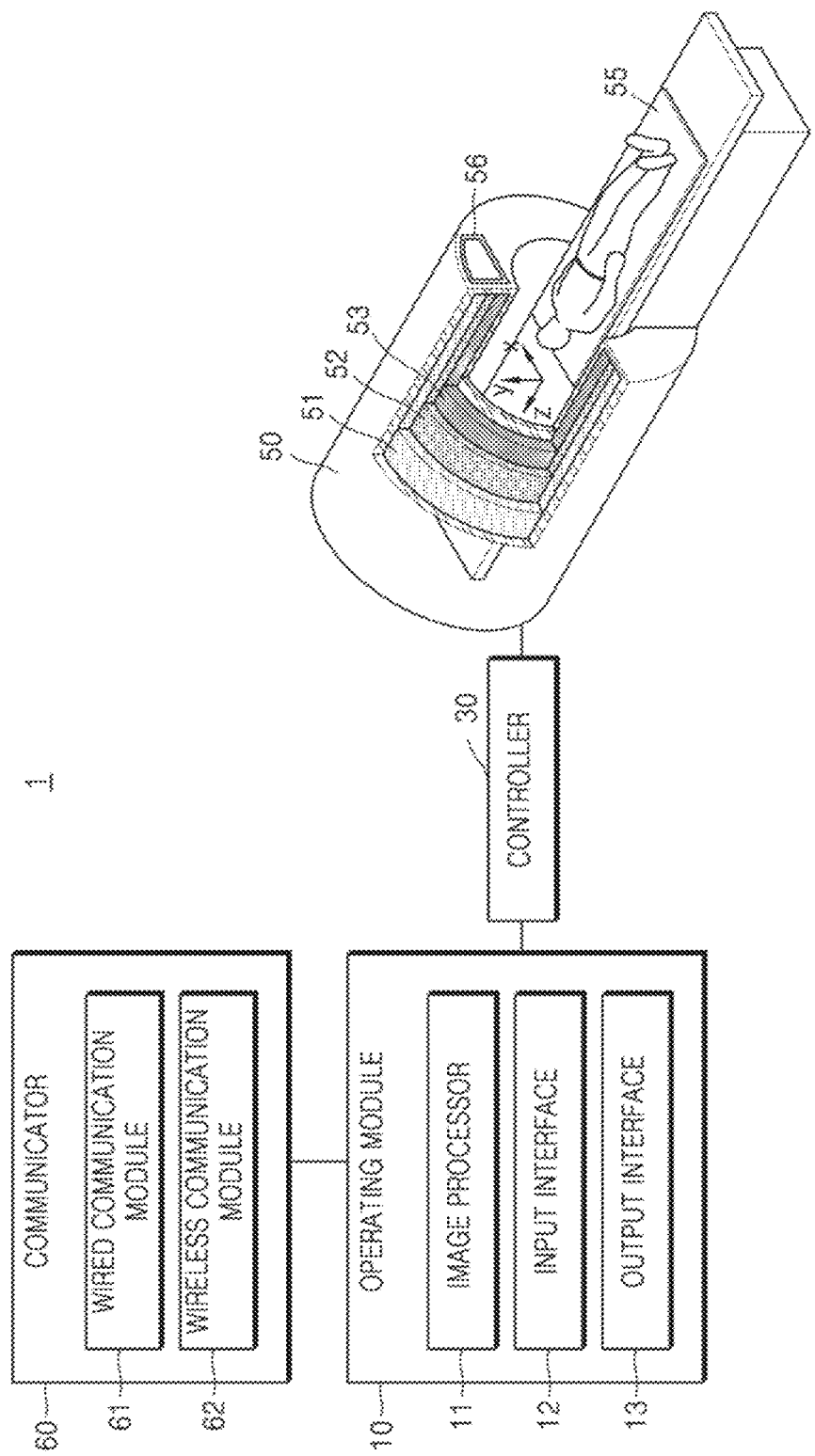
FIG. 8 is a schematic diagram of an MRI system.

FIG. 8 is a schematic diagram of an MRI system 1.

Referring to FIG. 8, the MRI system 1 may include an operator module 10, a controller 30, and a scanner 50. The controller 30 may be independently implemented as shown in FIG. 8. Alternatively, the controller 30 may be separated into a plurality of sub-components and incorporated into the operator module 10 and the scanner 50 in the MRI system 1. Operations of the components in the MRI system 1 will now be described in detail.

The scanner 50 may be formed to have a cylindrical shape (e.g., a shape of a bore) having an empty inner space into which an object may be inserted. A static magnetic field and a gradient magnetic field are created in the inner space of the scanner 50, and an RF signal is emitted toward the inner space.

The scanner 50 may include a static magnetic field generator 51, a gradient magnetic field generator 52, an RF coil unit 53, a table 55, and a display 56. The static magnetic field generator 51 creates a static magnetic field for aligning magnetic dipole moments of atomic nuclei of the object in a direction of the static magnetic field. The static magnetic field generator 51 may be formed as a permanent magnet or superconducting magnet using a cooling coil.

The gradient magnetic field generator 52 is connected to the controller 30 and generates a gradient magnetic field by applying a gradient to a static magnetic field in response to a control signal received from the controller 30. The gradient magnetic field generator 52 includes X, Y, and Z coils for generating gradient magnetic fields in X-, Y-, and Z-axis directions crossing each other at right angles and generates a gradient signal according to a position of a region being imaged so as to differently induce resonance frequencies according to regions of the object.

The RF coil unit 53 connected to the controller 30 may emit an RF signal toward the object in response to a control signal received from the controller 30 and receive an MR signal emitted from the object. The RF coil unit 53 may transmit, toward atomic nuclei of the object having precessional motion, an RF signal having the same frequency as that of the precessional motion, stop transmitting the RF signal, and then receive an MR signal emitted from the object.

The RF coil unit 53 may be formed as a transmitting RF coil for generating an electromagnetic wave having an RF corresponding to the type of an atomic nucleus, a receiving RF coil for receiving an electromagnetic wave emitted from an atomic nucleus, or one transmitting/receiving RF coil serving both functions of the transmitting RF coil and receiving RF coil. Furthermore, in addition to the RF coil unit 53, a separate coil may be attached to the object. Examples of the separate coil may include a head coil, a spine coil, a torso coil, and a knee coil according to a region being imaged or to which the separate coil is attached.

The display 56 may be disposed outside and/or inside the scanner 50. The display 56 is also controlled by the controller 30 to provide a user or the object with information related to medical imaging.

Furthermore, the scanner 50 may include an object monitoring information acquisition unit configured to obtain and transmit monitoring information about a state of the object. For example, the object monitoring information acquisition unit (not shown) may obtain monitoring information related to the object from a camera (not shown) for imaging images of a movement or position of the object, a respiration measurer (not shown) for measuring the respiration of the object, an ECG measurer for measuring the electrical activity of the heart, or a temperature measurer for measuring a temperature of the object and transmit the obtained monitoring information to the controller 30. The controller 30 may in turn control an operation of the scanner 50 based on the monitoring information. Operations of the controller 30 will now be described in more detail.

The controller 150 may control overall operations of the X-ray apparatus 50.

The controller 30 may control a sequence of signals formed in the scanner 50. The controller 30 may control the gradient magnetic field generator 52 and the RF coil unit 53 according to a pulse sequence received from the operator module 10 or a designed pulse sequence.

A pulse sequence may include all pieces of information required to control the gradient magnetic field generator 52 and the RF coil unit 53. For example, the pulse sequence may include information about a strength, a duration, and application timing of a pulse signal applied to the gradient magnetic field generator 52.

The controller 30 may control a waveform generator (not shown) for generating a gradient wave, i.e., an electrical pulse according to a pulse sequence and a gradient amplifier (not shown) for amplifying the generated electrical pulse and transmitting the same to the gradient magnetic field generator 52. Thus, the controller 30 may control formation of a gradient magnetic field by the gradient magnetic field generator 52.

The controller 30 may control an operation of the RF coil unit 53. For example, the controller 30 may supply an RF pulse having a resonance frequency to the RF coil unit 30 that emits an RF signal toward the object, and receive an MR signal received by the RF controller 53. In this case, the controller 30 may adjust emission of an RF signal and reception of an MR signal according to an operating mode by controlling an operation of a switch (e.g., a T/R switch) for adjusting transmitting and receiving directions of the RF signal and the MR signal based on a control signal.

The controller 30 may control a movement of the table 55 where the object is placed. Before imaging is performed, the controller 30 may previously move the table 55 in accordance with an imaging part of the object.

The controller 30 may also control the display 56. For example, the controller 30 control the on/off state of the display 56 or a screen to be output on the display 56 according to a control signal.

The controller 30 may be formed as an algorithm for controlling operations of the components in the MRI system 1, a memory (not shown) for storing data in the form of a program, and a processor for performing the above-described operations by using the data stored in the memory. In this case, the memory and the processor may be implemented as separate chips. Alternatively, the memory and processor may be incorporated into a single chip.

The operator module 10 may control overall operations of the MRI system 1 and include an image processor 11, an input interface 12, and an output interface 13.

The image processor 11 may control the memory to store an MR signal received from the controller 30, and generate image data with respect to the object from the stored MR signal by applying an image reconstruction technique by using an image processor.

For example, when a k space (for example, also referred to as a Fourier space or a frequency space) of the memory is filled with digital data to complete k space data, the image processor 11 may reconstruct image data from the k space data by applying various image reconstruction techniques (e.g., by performing inverse Fourier transform on the k space data) by using the image processor.

Furthermore, the image processor 11 may perform various signal processing operations on MR signals in parallel. For example, the image processor 62 may perform a signal process on a plurality of MR signals received by a multi-channel RF coil in parallel so as to rearrange the plurality of MR signals into image data. Meanwhile, the image processor 11 may store not only the image data in the memory, or the controller 30 may store the same in an external server via a communicator 60 as will be described below.

The input interface 12 may receive, from the user, a control command for controlling the overall operations of the MRI system 1. For example, the input interface 12 may receive, from the user, object information, parameter information, a scan condition, and information about a pulse sequence. The input interface 12 may be a keyboard, a mouse, a track ball, a voice recognizer, a gesture recognizer, a touch screen, or any other input interface.

The output interface 13 may output image data generated by the image processor 11. The output interface 13 may also output a user interface (UI) configured so that the user may input a control command related to the MRI system 1. The output interface 13 may be formed as a speaker, a printer, a display, or any other output interface.

Furthermore, although FIG. 8 shows that the operator module 10 and the controller 30 are separate components, the operator module 10 and the controller 30 may be included in a single device as described above. Furthermore, processes respectively performed by the operator module 10 and the controller 30 may be performed by another component. For example, the image processor 11 may convert an MR signal received from the controller 30 into a digital signal, or the controller 30 may directly perform the conversion of the MR signal into the digital signal.

The MRI system 1 may further include a communicator 60 and be connected to an external device (not shown) such as a server, a medical apparatus, and a portable device (e.g., a smartphone, a tablet PC, a wearable device, etc.) via the communicator 60.

The communicator 60 may include at least one component that enables communication with an external device. For example, the communicator 60 may include at least one of a local area communication module (not shown), a wired communication module 61, and a wireless communication module 62.

The communicator 60 may receive a control signal and data from an external device and transmit the received control signal to the controller 30 so that the controller 30 may control the MRI system 1 according to the received signal.

Alternatively, by transmitting a control signal to an external device via the communicator 60, the controller 30 may control the external device according to the control signal.

For example, the external device may process data of the external device according to a control signal received from the controller 30 via the communicator 60.

A program for controlling the MRI system 1 may be installed on the external device and may include instructions for performing some or all of the operations of the controller 30.

The program may be preinstalled on the external device, or a user of the external device may download the program from a server providing an application for installation. The server providing an application may include a recording medium having the program recorded thereon.

The above-described embodiments of the disclosure may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

While embodiments of the disclosure have been particularly shown and described with reference to the accompanying drawings, it will be understood by those of ordinary skill in the art that various changes in form and details may be made therein without departing from the spirit and scope of the inventive concept as defined by the appended claims. The disclosed embodiments should be considered in descriptive sense only and not for purposes of limitation.

The invention claimed is:

1. A magnetic resonance imaging (MRI) apparatus for obtaining a water-fat separation image, the MRI apparatus comprising:
a controller configured to
obtain first partial k-space data, second partial k-space data, and third partial k-space data, respectively, based on a first partial echo signal, a second partial echo signal, and a third partial echo signal, which are magnetic resonance signals corresponding to a plurality of echo times with respect to an object,
obtain first reconstruction image data, second reconstruction image data, and third reconstruction image data with respect to the object, respectively, based on the first partial k-space data, the second partial k-space data, and the third partial k-space data, and
obtain first water image data, first fat image data, and first phase image data of the object, respectively, based on the first reconstruction image data, the second reconstruction image data, and the third reconstruction image data, by using a Dixon technique, such that k-space data corresponding to each of the first water image data and the first fat image data obtained using the Dixon technique has an origin symmetric law equal to or greater than a certain value with respect to a center of a k-space.

2. A method of obtaining a water-fat separation image, the method comprising:
obtaining first partial k-space data, second partial k-space data, and third partial k-space data, respectively, based on a first partial echo signal, a second partial echo signal, and a third partial echo signal, which are magnetic resonance signals corresponding to a plurality of echo times with respect to an object;
obtaining first reconstruction image data, second reconstruction image data, and third reconstruction image data with respect to the object, respectively, based on the first partial k-space data, the second partial k-space data, and the third partial k-space data; and
obtaining first water image data, first fat image data, and first phase image data of the object, respectively, based on the first reconstruction image data, the second reconstruction image data, and the third reconstruction image data, by using a Dixon technique, such that k-space data corresponding to each of the first water image data and the first fat image data obtained using the Dixon technique has an origin symmetric law equal to or greater than a certain value with respect to a center of a k-space.

3. The MRI apparatus of claim 1, further comprising:
an RF coil configured to irradiate an RF excitation pulse to the object and receive the first partial echo signal, the second partial echo signal, and the third partial echo signal from the object.

4. The MRI apparatus of claim 1, wherein the controller is further configured to obtain first k-space data, second k-space data and third k-space data of the object corresponding to the plurality of echo times, based on the first water image data, the first fat image data, the first phase image data, the first partial k-space data, the second partial k-space data, and the third partial k-space data.

5. The MRI apparatus of claim 4, wherein the controller is further configured to
obtain first water k-space data and first fat k-space data respectively corresponding to the first water image data and the first fat image data,
cause the first water k-space data and the first fat k-space data to be origin symmetric with respect to a center of a k-space and obtain the origin symmetric first water k-space data and the origin symmetric first fat k-space data, and
obtain the first k-space data, the second k-space data and the third k-space data respectively based on the origin symmetric first water k-space data, the origin symmetric first fat k-space data, and the first phase image data.

6. The MRI apparatus of claim 5, wherein the controller is further configured to
- obtain k-space data corresponding to each of the plurality of echo times based on the origin symmetric first water k-space data, the origin symmetric first fat k-space data, and the first phase image data, and
- obtain the first k-space data, the second k-space data and the third k-space data by replacing some of the k-space data with the first partial k-space data, the second partial k-space data, and the third partial k-space data.

7. The MRI apparatus of claim 6, wherein the controller is further configured to obtain second water image data, second fat image data and second phase image data with respect to the object respectively based on the first k-space data, the second k-space data, and the third k-space data, by using the Dixon technique.

8. The MRI apparatus of claim 7, wherein the controller is further configured to
- obtain at least one of k-space data corresponding to the second water image data and k-space data corresponding to the second fat image data,
- determine whether an origin symmetric law of at least one of the k-space data corresponding to the second water image data and the k-space data corresponding to the second fat image data is equal to or less than a certain threshold value,
- update the k-space data based on the second water image data, the second fat image data, and the second phase image data when the origin symmetric law is equal to or less than the certain threshold value, and
- update the first k-space data, the second k-space data, and the third k-space data based on the updated k-space data, the first partial echo signal, the second partial echo signal, and the third partial echo signal.

9. The MRI apparatus of claim 1, wherein the controller is further configured to obtain at least one of a first water emphasis image, a first fat emphasis image, and a first phase image, based on the first water image data, the first fat image data, and the first phase image data.

10. The MRI apparatus of claim 9, further comprising:
a display displaying at least one of the obtained first water emphasis image, first fat emphasis image, and first phase image.

11. The method of claim 2, further comprising:
irradiating an RF excitation pulse to the object and receiving the first partial echo signal, the second partial echo signal, and the third partial echo signal from the object.

12. The method of claim 2, wherein the obtaining of the first water image data, the first fat image data, and the first phase image data of the object comprises:
obtaining first k-space data, second k-space data and third k-space data of the object corresponding to the plurality of echo times, based on the first water image data, the first fat image data, the first phase image data, the first partial k-space data, the second partial k-space data, and the third partial k-space data.

13. The method of claim 12, wherein the obtaining of the first k-space data, the second k-space data and the third k-space data of the object comprises:
- obtaining first water k-space data and first fat k-space data respectively corresponding to the first water image data and the first fat image data;
- causing the first water k-space data and the first fat k-space data to be origin symmetric with respect to a center of a k-space and obtain the origin symmetric first water k-space data and the origin symmetric first fat k-space data; and
- obtaining the first k-space data, the second k-space data and the third k-space data respectively based on the origin symmetric first water k-space data, the origin symmetric first fat k-space data, and the first phase image data.

14. The method of claim 13, wherein the obtaining of the first k-space data, the second k-space data and the third k-space data comprises:
- obtaining k-space data corresponding to each of the plurality of echo times based on the origin symmetric first water k-space data, the origin symmetric first fat k-space data, and the first phase image data; and
- obtaining the first k-space data, the second k-space data and the third k-space data by replacing some of the k-space data with the first partial k-space data, the second partial k-space data, and the third partial k-space data.

15. The method of claim 14, further comprising:
obtaining second water image data, second fat image data and second phase image data with respect to the object respectively based on the first k-space data, the second k-space data, and the third k-space data, by using the Dixon technique.

16. The method of claim 15, further comprising:
- obtaining at least one of k-space data corresponding to the second water image data and k-space data corresponding to the second fat image data;
- determining whether an origin symmetric law of at least one of the k-space data corresponding to the second water image data and the k-space data corresponding to the second fat image data is equal to or less than a certain threshold value;
- updating the k-space data based on the second water image data, the second fat image data, and the second phase image data when the origin symmetric law is equal to or less than the certain threshold value; and
- updating the first k-space data, the second k-space data, and the third k-space data based on the updated k-space data, the first partial echo signal, the second partial echo signal, and the third partial echo signal.

17. The method of claim 2, wherein the obtaining of the first water image data, the first fat image data, and the first phase image data further comprises:
obtaining at least one of a first water emphasis image, a first fat emphasis image, and a first phase image, respectively based on the first water image data, the first fat image data, and the first phase image data.

18. A computer program product comprising a non-transitory computer readable recording medium having recorded thereon a program for executing the method of claim 2 on a computer.

* * * * *